United States Patent [19]

Jach et al.

[11] Patent Number: 5,008,908

[45] Date of Patent: Apr. 16, 1991

[54] DIFFRACTION DEVICE WHICH DETECTS THE BRAGG CONDITION

[75] Inventors: Terrence J. Jach, Washington, D.C.; Jon C. Geist, Olney, Md.; Gary P. Carver, Ijamsville, Md.; Donald B. Novotny, Bethesda, Md.

[73] Assignee: The United States of America as represented by the Secretary of Commerce, Washington, D.C.

[21] Appl. No.: 282,243

[22] Filed: Dec. 9, 1988

[51] Int. Cl.$^5$ .............................................. G01N 23/20
[52] U.S. Cl. .................................... 378/70; 378/84; 378/207; 250/390.09
[58] Field of Search .................................. 378/70–73, 378/84, 85, 51, 207; 250/370.01, 370.09, 371, 311, 397; 252/301.4 R, 301.5, 301.6 R

[56] References Cited

U.S. PATENT DOCUMENTS

| | | | |
|---|---|---|---|
| 2,619,600 | 11/1952 | Hamacher | 378/73 |
| 2,816,234 | 12/1957 | Ellis | 378/70 |
| 3,417,026 | 12/1968 | Arthur | 252/301.6 R |
| 3,642,651 | 2/1972 | Marboe et al. | 252/301.4 R |
| 3,772,520 | 11/1973 | Varker | 250/311 |
| 3,833,827 | 9/1974 | Shaffer | 252/301.5 |
| 4,261,771 | 4/1981 | Dingle et al. | 378/84 |
| 4,447,305 | 5/1984 | Heindl et al. | 252/301.4 R |
| 4,751,148 | 6/1988 | Popma et al. | 252/301.4 R |
| 4,785,470 | 11/1988 | Wood et al. | 378/84 |

OTHER PUBLICATIONS

Afanas'ev, et al., "Diffraction of X Rays and Electrophysical Properties of Crystals", JETP Lett., vol. 28, No. 6, American Institute of Physics, Sept. 20, 1978, pp. 321–324.

Afanas'ev, et al., "Photoelectric Phenomena Accompanying Diffraction of X Rays in Semiconducting Crystals", Sov. Phys. Solid State 24(9), American Institute of Physics, Sept. 1982, pp. 1473–1476.

Bedzyk, et al., "Detection of Interference Phenomena in Standing X-Ray waves in studying the internal photoeffect in a Schottky barrier", Sov. Phys. Dokl. 30(5), American Institute of Physics, May 1985, pp. 381–382.

Goossen, et al., "Grating Enhancement of Quantum Well Detector Response", Appl. Phys. Lett., 53(12), American Institute of Physics, Sept. 19, 1988, pp. 1027–1029.

Annaka, et al., "Variations in X-Ray Fluorescence from GaAs and Photocurrent in CdS due to Standing Waves of X-Rays", Japanese Journal of applied Physics, vol. 23, No. 12, Dec. 1984, pp. 1637–1639.

Primary Examiner—Carolyn E. Fields
Assistant Examiner—David P. Porta
Attorney, Agent, or Firm—Alvin J. Englert; David A. Blumenthal; Richard Torczon

[57] ABSTRACT

A periodic scattering array is used to diffract electromagnetic radiation or massive particles of specific wavelength and energy. A detector sutiable to the radiation or particles is integrated into the surface or bulk of the array. The detector is configured so as to not perturb the diffraction resolution of the array.

12 Claims, 5 Drawing Sheets

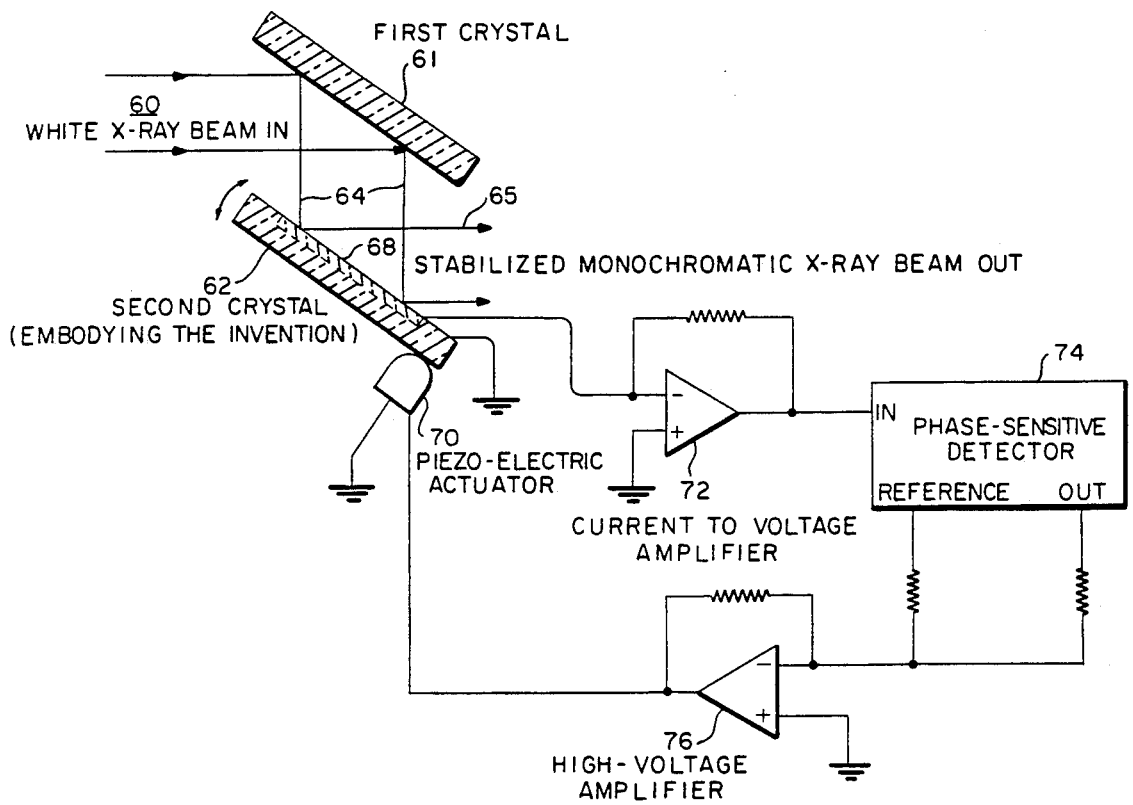
FIG. 7
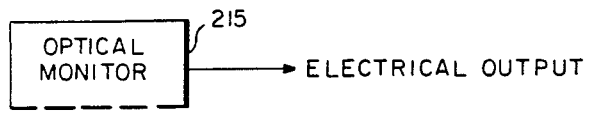
FIG. 8
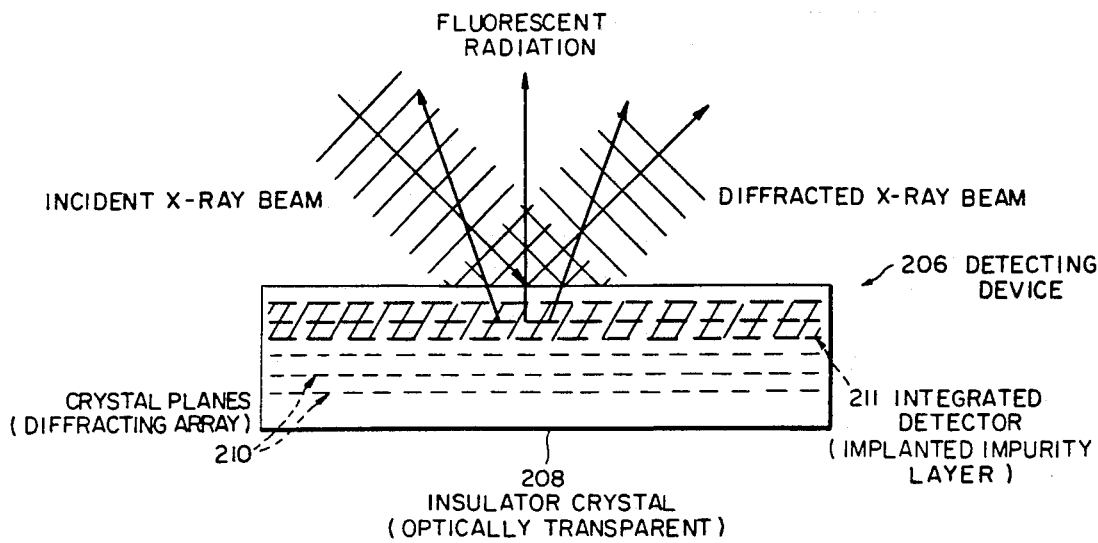

DIFFRACTION DEVICE WHICH DETECTS THE BRAGG CONDITION

Background of the Invention

Electromagnetic radiation (photons) and massive elementary particles (e.g. electrons, neutrons) are characterized by wavelike behavior having an associated wavelength. Since there is a unique relationship between the wavelength and the energy of the particle, devices which select particles of a certain wavelength are commonly used as energy selecting devices (monochromators). One of the most common means of selecting particles by wavelength is diffraction, a process by which the particles are scattered by a periodic array of scatterers. For incident electromagnetic radiation of any given wavelength, the coherent sum of scattered radiation from a periodic array of scatterers is highly maximized at certain angles of incidence with respect to the alignment of the array. An analogous phenomenon holds for massive particles. Such an angle is known as a Bragg angle, and the achievement of the diffraction condition is known as the Bragg Condition. The diffraction geometry referred to hereafter is that where the coherently scattered beam exits from the same surface on which the beam was incident, thereby appearing to be reflected from the surface.

The quality of a diffraction device is defined here by the achievement of its theoretical minimum limits for a narrow angular range over which diffraction occurs and high apparent reflectivity or transmission of the diffracted radiation at the Bragg Condition.

For electromagnetic radiation in the energy range 1–800 electron volts (eV), the array of choice is a reflecting surface ruled with periodic grooves, known as a diffraction grating. For electromagnetic radiation in the energy range 800 eV and above, the array of choice is the lattice of atoms in a single crystal which can be taken, especially for purposes of claim interpretation, to include an artificially layered material such as a multilayer surface produced by thin film techniques. A single crystal is also the usual diffracting agent for massive particles because the spacing of atomic planes in a crystal is appropriate for diffraction, given their wavelength over a wide range of energy.

It is common practice to monitor the Bragg Condition by detecting radiation or particles diffracted by the periodic device. This is done by putting a detector downstream of the diffraction device to intercept a portion of the diffracted beam which results when the periodic array is oriented to the Bragg Condition.

Summary of the Invention

If a beam of monochromatic radiation or particles strikes a crystal, it can be shown that the depth at which the radiation penetrates into the crystal varies systematically as the incidence angle is brought into the vicinity of the correct angle at which diffraction will occur, otherwise known as the Bragg Condition or Bragg angle. Furthermore, the intensity of radiation which penetrates the crystal undergoes a variation as well. This should be evident from the fact that away from the Bragg Condition the radiation penetrates the crystal and is absorbed, while at the Bragg Condition most of the radiation is reflected by the crystal.

Therefore, it is an object of the present invention to provide a device which is able to monitor the intensity and distribution of radiation absorbed inside the diffracting array by means of detectors integrated into the surface or bulk of the array itself. The detectors are of such a nature as not to disturb the periodic scattering properties of the array.

The changes in radiation intensity with depth inside the periodic array of scatterers which occurs as it is aligned to the Bragg Condition are directly detectable by the correlated variation in absorbed radiation and its variation with depth. The intensity changes are observed as signals from the integrated detectors. The concept is applicable to cases where diffraction is the result of scattering from a crystal or a grating, and to massive particles as well as electromagnetic radiation, since absorption losses correlated to the diffraction condition occur for either of these cases.

Brief Description of the Drawings

The invention will now be described more fully with reference to several embodiments and the drawings, in which:

FIG. 7 shows a typical embodiment wherein two crystals are aligned to diffract sequentially the same x-ray beam; and FIG. 8 illustrates another embodiment of the invention which employs an insulating crystal.

Detailed Description of the Preferred Embodiments

Figure 1:
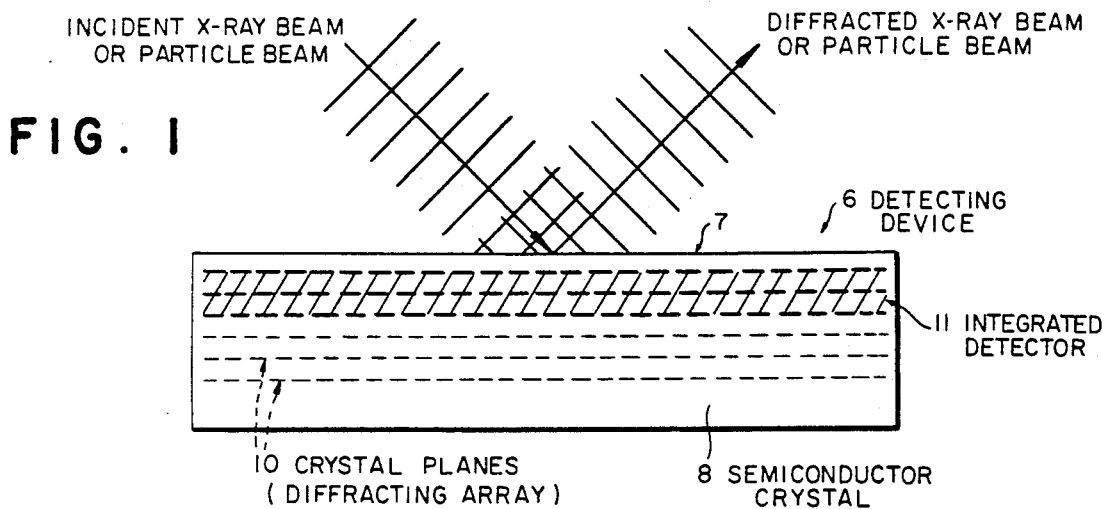
FIG. 1 shows the incorporation of a detector, in this case a photodiode p-n junction, into the bulk of a periodic diffraction array, in this case a semiconductor crystal.

Referring now to FIG. 1, the diffraction detecting device 6 performing the diffraction of x-rays in the present invention comprises a semiconductor crystal 8 having a plurality of crystal planes 10 serving as a diffracting array. An integrated detector 11, as an example and not by way of limitation, comprises a semiconductor diode having a p-n junction which is integrated at a certain depth into the bulk of the diffracting crystal 8. The diode detector 11 is produced by a process which leaves the diffracting array, i.e., the crystal, unperturbed by strains which would affect its diffraction characteristics. The diffraction detecting device 6 may typically respond to x-rays in the energy range of 2–10 keV.

The detection is accomplished by the separation and collection of electron-hole pairs ultimately produced by x-rays penetrating into the crystal. If a monochromatic beam of x-rays strikes the device as shown in FIG. 1, the x-rays penetrate into the crystal 8 with an exponentially decaying intensity, characterized by an extinction length, defined normal to the crystal surface 7. See, for example, B. W. Batterman et al, *Reviews of Modern Physics*, Vol. 36, p.p. 681–717 (1964), incorporated herein by reference. Absorption processes in the crystal 8 are locally proportional to the intensity of the x-rays. The absorption of an x-ray photon creates a high energy photoelectron which ionizes valence band electrons into the conduction band by inelastic collisions, resulting in a large number of electron-hole pairs. See, for example, A. J. Tuzzolino, *Physical Review*, Vol. 134, p. A205–A213 (1964), incorporated herein by reference. The electric field which exists in the p-n junction diffused into the bulk of the diffracting crystal serves to separate the electrons and holes, which are the source of the detected photovoltage or photocurrent, depending on the external circuit to which the junction is connected.

Figure 2:
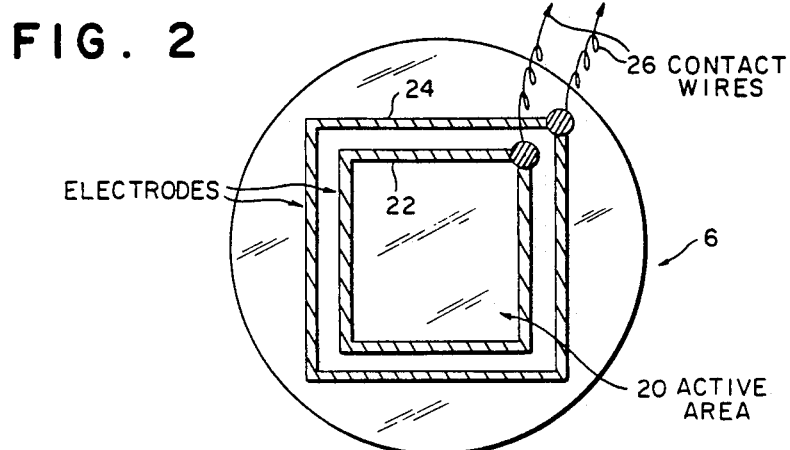
FIG. 2 shows the top view of an embodiment of the device consisting of a p-n junction in a semiconducting crystal.

FIG. 2 shows the top view of a working prototype of the diffraction detecting device 6. The device contains an x-ray sensitive detection region or active area 20, about 1 cm×1 cm in size. This area 20 consists of a planar p-n junction which may be formed, for example, by starting with an n-type silicon diffraction crystal and doping with a p-type dopant for conversion to a p-type semiconductor. On the p-type doped layer a patterned conductor serving as electrode 22 is formed which makes electrical contact to the p-type surface region of area 20. An outer conductor ring 24 surrounds, but does not touch, the p-type detection area 20 so as to minimize surface leakage current. This conductive ring 24 also serves as an electrode and makes electrical contact to the n-type bulk material of the diffraction crystal 8. Contact wires 26 extend from each of the electrodes 22 and 24.

Figure 3:
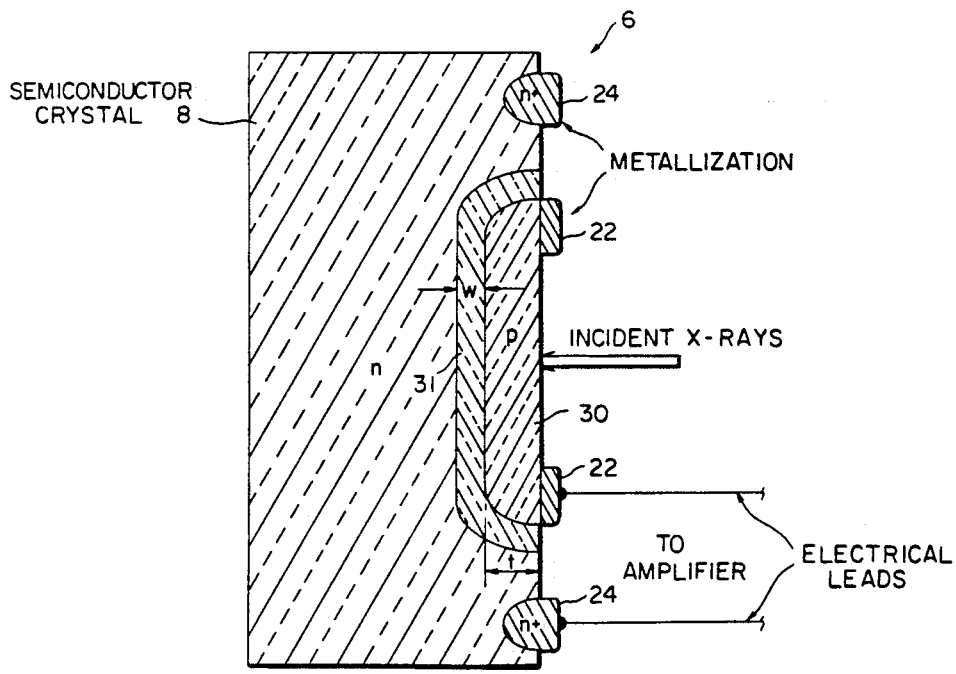
FIG. 3 shows a cross-sectional view of an embodiment of the device consisting of a p-n junction diffused into a semiconducting crystal.

FIG. 3 shows a sectional view of the detecting device 6. The dopant distribution in the p-type region 30 follows a gaussian profile in the crystal. The thickness of the p-type region is t. The p-type region is separated from the n-type region by the depletion region of width w. Depending upon the exact details of the processing, the detection device can be made to separate and collect (thereby converting to a photocurrent) all of the electron-hole pairs that are created in the depletion region and in the n-type region, while separating none of the electron-hole pairs that are created in the front half of the p-type region. This is desirable because, as the diffracting crystal is rotated to the Bragg Condition for x-rays of a particular energy, the reflectance of the crystal increases from a negligible level to nearly unity, and the extinction depth decreases by about an order of magnitude. In a device with the properties just described, both the increase in reflectance and the decrease in extinction depth will contribute to a reduction of photocurrent as the Bragg Condition is achieved.

To make this concrete, consider diffraction of 8 keV x-rays from the (111) planes to a silicon crystal, in which case the extinction length decreases from about 17 $\mu$m to 0.74 $\mu$m as the Bragg Condition is achieved. The overall thickness of the diffracting crystal is preferably at least 2.5 mm to preclude flexure of the crystal that would broaden the angular width of the Bragg reflection by distortions of the crystal lattice. The p-type dopant distribution preferably follows a gaussian profile which peaks at a point about 0.5 $\mu$m within the p-type region (which would require that t be greater than or approximately equal to 2 $\mu$m). The depletion width w is preferably greater than or equal to 3 $\mu$m, and the diffusion length of the minority carriers in the n-type region is preferably greater than 20 $\mu$m. Finally, the front surface of the silicon crystal is preferably unpassivated or uncoated, and therefore has a very large recombination velocity.

When the 8 keV x-rays are incident on the crystal near, but not at the angle that satisfies the Bragg Condition, virtually all of the x-rays penetrate the crystal and 90% of the x-ray intensity penetrates to a depth t. Between 70% and 100% of the radiation which reaches that depth will contribute to the photocurrent, depending on the details of the processing.

When the 8 keV x-rays are incident on the crystal such that they do satisfy the Bragg Condition, at least 90% of the x-rays are reflected from the crystal, and the intensity at the depth t is less than 12% of the surface intensity. Electron-hole pairs caused by absorption of x-rays at a depth less than t do not contribute to the photocurrent because they recombine at the front surface of the crystal before they can be separated. The photocurrent collected at the Bragg Condition is therefore significantly lower.

The p-n junction is formed in a single crystal semiconductor in such a manner that it does not significantly distort the crystal lattice of the original semiconductor and ruin its diffraction quality. Details in the fabrication of the junction which could distort the crystal lattice include dopant atoms of a different size from the host semiconductor atoms, and overlayers such as metals or oxides with a different lattice constant from the semiconductor substrate. Depending on the size of the dopant atoms, there is a maximum surface concentration of dopant atoms which can be tolerated without degradation of the crystal due to strain from its natural resolution as a diffraction device.

Any monocrystalline semiconductor can be used for which the above criteria can be achieved. These include, but are not limited to: silicon, germanium, zinc selenide, gallium arsenide, and indium antimonide. The detector could equally well be fabricated on a p-type substrate with an n-type doped layer forming the surface junction layer.

An important property of the detecting device 6 is that the dopants used to form the p-n junction be at a concentration large enough to form the electric field at the depletion region, while at the same time small enough so that the diffracting properties determined by the regularity of the semiconductor crystal lattice not be distorted. In a preferred embodiment it was established that the boron dopant used to form the p-n junction be at a concentration of less than $10^{19}$ atoms/cm$^3$ in order to satisfy the distortion criteria above. No oxide layer or other overlay was left on the device.

It is also important to make electrical contacts to the active area 20 and non-active, substrate regions of the crystal 8 under the same constraints, e.g., formation of electrodes 22 and 24 should not distort the active region of the crystal lattice.

Figure 4:
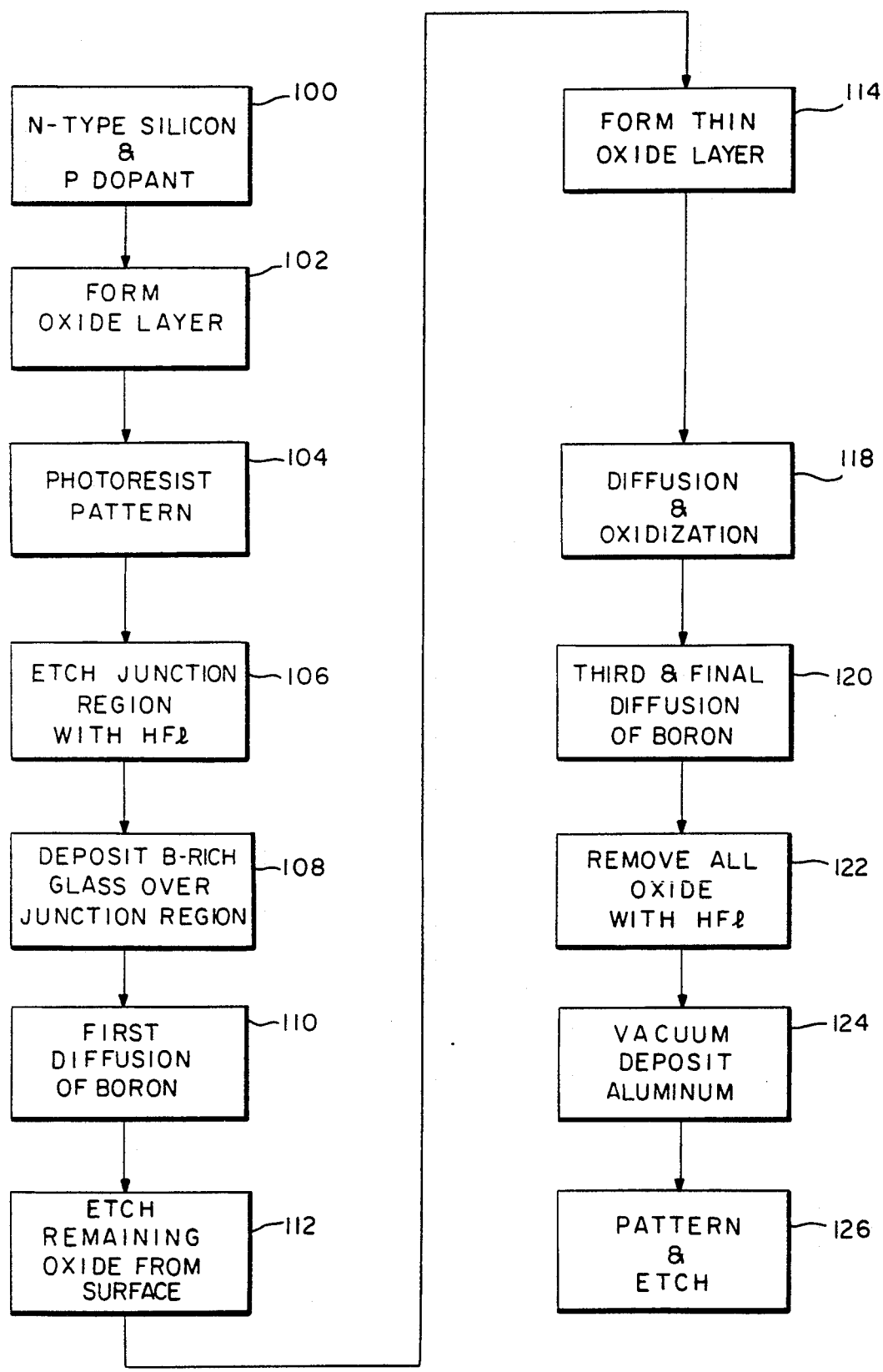
FIG. 4 is a flowchart showing the fabrication process of the diffracting device in accordance with the invention.

Details of the fabrication process used to construct the prototype detector are described in reference to FIG. 4. In step 100, a monocrystalline slice of n-type silicon, with its surface parallel to the (111) crystal planes, is doped with phosphorous to produce a uniform n-type impurity concentration in the silicon of about $10^{15}$ atoms/cm$^3$ of phosphorus. Depending on the extinction depth of the x-rays, bulk impurity concentrations of as little as $10^{10}$ or as great as $10^{16}$ atoms/cm$^3$ would be appropriate.

In step 102, an oxide layer of about 300 nm thickness was formed on the surface of the diffracting crystal by wet oxidation of the silicon. This was done by heating the silicon surface to 1050° C. at partial pressures of 640 torr of steam and 120 torr oxygen. In steps 104 and 106, the oxide layer was removed from selected areas to be doped using common photolithographic techniques followed by etching in buffered hydrofluoric acid. See, for example, S.K. Ghandi *VLSI Fabrication Principles*, John Wiley & Sons, New York, 1983, Chapter 10, incorporated herein by reference. The oxide layer remained in all other regions as a substrate mask. The junction area was deposited by p-type boron dopant in a three-step process. See, for example, N.H. Ditrik et al *Solid State Technology*, Vol. 23, July 1980, incorporated herein by reference. In step 108, a boron-rich glass was deposited on the surface at a temperature of 800° C. at, and in step 110, the boron was diffused into the surface at 825° using a diffusion constant-time (Dt) product calculated to give a total diffusion of about $3 \times 10^{13}$ atoms/cm$^2$. Depending on the extinction depth for which the device is to be optimized, a Dt-product could vary between $4 \times 10^{-11}$ and $4 \times 10^{-9}$ cm$^2$.

This initial diffusion was followed in step 112 by the removal, by hydrofluoric acid etch, of all the remaining oxide layers from the crystal surface. In step 114, another thin oxide layer of tens of nanometers thickness was formed by wet oxidation of the surface of the silicon at 750° C. in an atmosphere of steam and oxygen for a few minutes. The temperature was raised to 1050° C. In step 118, while diffusion was occurring, more oxide was formed on the crystal surface by introducing an atmosphere of steam and oxygen at the same partial pressures listed above for 18 minutes. Depending on the desired surface concentration at the end of the process, times of 15-20 minutes would be selected. Following this oxidation, the diffusion process was completed in step 120 at the same temperature in an atmosphere of nitrogen for a duration of 95 minutes.

The p-n junction depth thus produced was measured by the method of grooving and staining to be 0.54 μm. See, for example, A. S. Grove, *Physics and Technology of Semiconductor Devices*, J. Wiley & Sons, N.Y. 1967, Chapter 3. A preferred embodiment might have a junction which was even deeper. By measuring the sheet resistance of the surface it was determined that the process resulted in a surface concentration of $1.8 \times 10^{18}$ atoms/cm$^3$ of boron. See, for example, the measurement technique described in J.C. Irvin, *Bell System Technical Journal*, Vol. 41, P. 387–410 (1962), incorporated herein by reference. By choice of a range of times of 30 minutes to 5 hours, and a choice of temperatures in the range of 850° to 1100° C., a range of Dt-products is achieved which produce junction depths in the range of 0.1 μm to 10 μm, allowing for optimization to a wide range of extinction depths. By going to the upper range of Dt-products, the surface concentration is lowered to minimize strain in the lattice.

There is also the possibility of doping the backside of the diffraction crystal with heavier layers of n-type impurities than are present in the bulk of the crystal to decrease the effective electron-hole recombination rate in the n-type region.

The diffusion process was followed by removing all the oxide layers in hydrofluoric acid (step 122) and immediately vacuum-depositing a film of aluminum 700 nm thick on the boron-doped silicon surface (step 124). This film, which could range from 200 to 1000 nm thick, was lithographically patterned and etched (step 128) to form the electrode lines on the p-n junction region shown in FIG. 2. The patterned aluminum electrodes were micro-alloyed with the surface at 450° C. to make ohmic contacts with the surface. Ohmic contacts may include p-type or n-type additional doping in the crystal at the region of contact.

The preferred embodiment of the specific silicon crystal x-ray diffraction device consists of (1) a thick, oriented, strain-free semiconductor single crystal with a narrow x-ray rocking curve, free of dislocations or other defects, (b 2) a moderately doped, planar, annealed, diffused, ion-implanted, or epitaxial layer p-n junction that underlies an area of the crystal surface on which the radiation to be diffracted will fall, at a depth which will take advantages of changes in the extinction length of the x-rays at the Bragg Condition, (3) two electrodes, one making ohmic contact to the p-type region of the crystal, the other making ohmic contact to the n-type region of the crystal, (4) an arrangement of the above electrodes to minimize surface leakage current between them, including, for example, a guard ring, (5)an arrangement of dopant density on the backside of type opposite to that on the front (but of comparable density and width) of the thick crystal in order to retard recombination of uncollected carriers.

The requirement that the detector fabrication not interfere with the x-ray diffraction function of the device was achieved by the following:

(1) A very low amount of impurity was initially diffused into the silicon surface which was coupled with steam oxidations of the surface at low and elevated temperature.

(2) The silicon dioxide layer used to mask boron diffusion and prevent it from doping the silicon substrate outside the p-n junction region was removed only from the detector side of the diffraction crystal. Oxide remained on all other surfaces of the silicon to protect it from diffusion.

(3) In the final step, all oxide layers were completely removed from the silicon. This minimized crystal strain caused by lattice mismatch between the oxide film and silicon substrate and also prevented x-ray scattering by the silicon dioxide overlayer.

Figure 5:
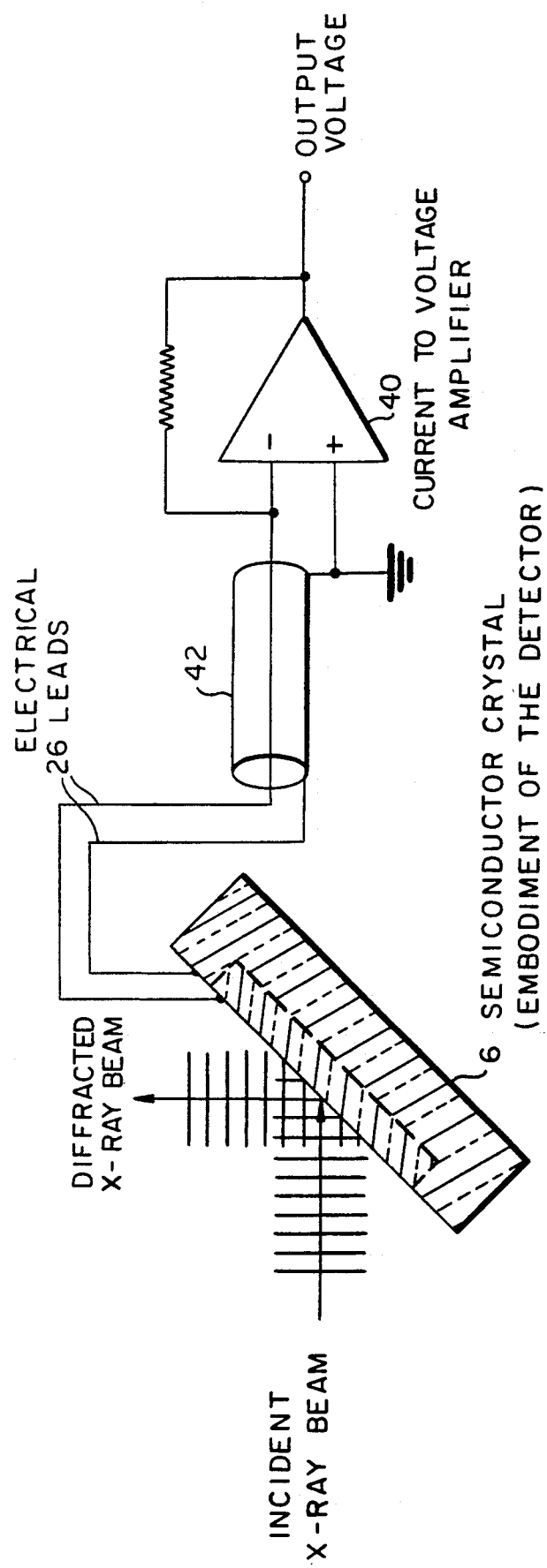
FIG. 5 shows the electrical circuit used to extract a photocurrent from a diode detector in a semiconductor crystal which is diffracting electromagnetic waves at x-ray energies.

FIG. 5 shows the manner in which the photocurrent produced by the device may be typically utilized to produce an indication of the diffraction condition of a monochromatic x-ray beam. An x-ray beam and the diffracted beam are shown together with detecting device 6. Detecting device 6 is connected to amplifier circuitry 40 by electrical leads 26 and shielded cable 42.

Figure 6:
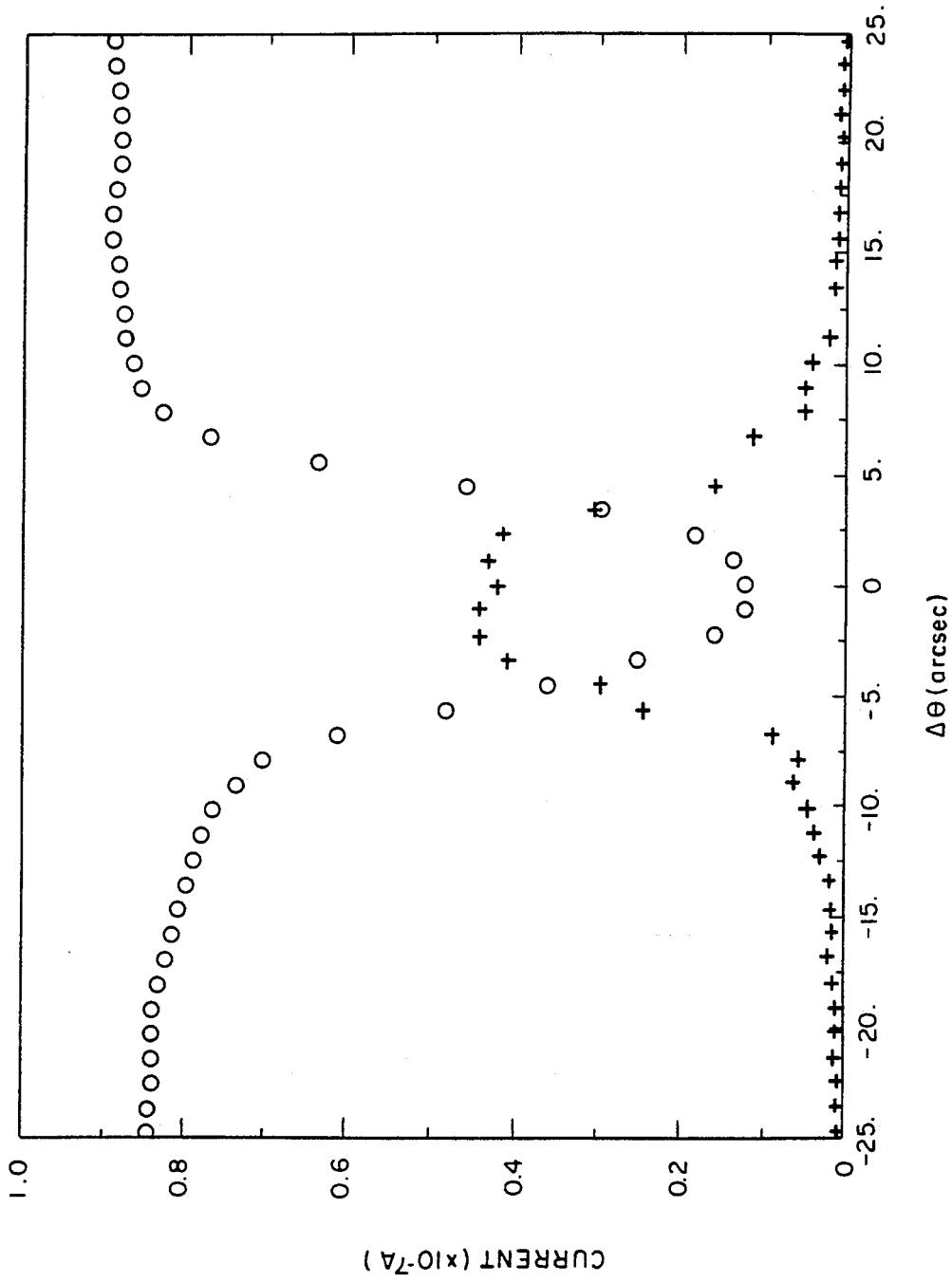
FIG. 6 shows plots of the output current of the detector incorporated into the bulk of a diffracting crystal and the intensity of the diffracted beam as a function of the orientation angle near the Bragg Condition.

FIG. 6 shows a typical photocurrent obtained from the device when irradiated with monochromatic x-rays at an energy of 8 keV. The figure shows the correlation between the diminution of the internally detected photocurrent represented by the symbol "o", with the onset of diffraction of the x-ray beam from the (111) lattice planes of the silicon crystal. The diffracted beam flux is represented by the symbol "+".

FIG. 7 shows a typical application of the device 6 in a feedback circuit of a double-crystal x-ray monochromator as used in an intense x-ray beam. The arrangement assures active alignment of the second monochromating crystal to the Bragg Condition despite changes during operation in the lattice constant between the first and second crystals due to heating of the first crystal by the intense x-ray beam. The embodiment shown includes first and second crystals 61, 62 which are aligned to diffract sequentially the same x-ray beam. An x-ray beam 60 is incident on the first crystal 61. Typically, the incident beam 60 contains all energies of electromagnetic radiation. Beam 64 leaving the first crystal is of an energy within a narrow band that is passed by the diffraction process at a given Bragg angle and is diffracted from the second crystal 62 back into a path 65 nearly parallel to the path of the incident beam. Differences in crystal composition, temperature, or lattice alignment require on active system to maintain the second crystal angle oriented to pass the beam at the Bragg angle from the first crystal. An integral detector 68, structured and fabricated in accordance with the teachings of the invention, detects the diffraction condition in the second crystal 62 and is utilized to generate the input signal to the feedback circuit. The monochromator is otherwise of a standard design presently used for x-ray research. The monochromator of this embodiment includes a piezo-electric actuator 70, a current to voltage amplifier 72, a phase-sensitive detector 74, and a high-voltage amplifier 76.

The principles of the embodiment described above represent a special case of a more general description of a preferred embodiment. For example, the device described above will function in the same manner for detecting the Bragg Condition during the diffraction of neutrons (massive particles) as it will for x-ray photons.

A more generalized embodiment of a diffraction device which detects the Bragg Condition consists of:
1. The diffraction device; and
2. A detector that lies within the portion of the diffraction device upon which the radiation to be detected falls, and which converts the radiation entering or penetrating the diffraction device into a signal (electrical, visible light, etc.).

In the ideal case,
i. the conversion efficiency of the detector as a function of depth in the diffraction device is tailored to the incident radiation by alterations in the detector fabrication process;
ii. the quality of the diffraction device with respect to the ability to diffract (as defined by the narrow angular range over which diffraction occurs and the high apparent reflectivity of the diffraction device at the Bragg Condition) is not reduced by the presence of the detector.
3. A means of collecting the absorption signal from the detector that transmits the signal to a measurement device. Examples are electrodes that make physical contact with the diffraction device, optical elements to collect emitted light, optical fibers, or electron detectors which detect x-ray photoelectrons escaping from the surface of the device.

FIG. 8 illustrates another embodiment of the invention in which an insulator is utilized as the detecting crystal. In this embodiment, detecting device 206 comprises an insulator crystal 208 which may include, for example, quartz, beryl or the like. Crystal planes 210 form a diffracting array for the incoming radiation beam of particles or x-rays. The crystal is implanted with an impurity layer forming an integrated detector 211. The impurity layer can be formed from a metal ion such as titanium, iron or the like, and the impurity layer can be diffused into the interior of the crystal 208 by heat diffusion using similar techniques as those described in connection with the semiconductor detector described above.

When the incoming radiation beam is absorbed in the crystal, i.e., at non-Bragg angle conditions, the radiation causes fluorescence in the impurity layer or region. This fluorescent radiation is measured by means of optical monitor 215, such as a photoelectric device, which produces an electric signal proportional to the intensity of the monitored radiation. When the incoming radiation is oriented such as to produce the Bragg Condition, the incident radiation beam will be diffracted with a minimal amount of radiation absorbed in the crystal. If the impurity layer is positioned deeper than the Bragg angle extinction depth, a minimum in the resulting fluorescent radiation beam will be detected when the Bragg Condition is satisfied.

It should be noted that the present invention has been disclosed in terms of preferred embodiments. The invention, however, is not intended to be limited thereto. For example, for both x-rays and particles, the p-n junction depth may be selected to be equal to the extinction depth at the Bragg angle and shorter than the extinction depth at angles other than the Bragg angle. Such an arrangement will result in a current maximum at the Bragg angle as opposed to the minimum shown in FIG. 6. Similarly, positioning the impurity region in the insulator crystal at a depth less than the Bragg angle extinction depth will result in a maximum in the fluorescent radiation output at the Bragg Condition.

What is claimed is:
1. A diffraction device comprising:
   (a) a semiconductor crystal having a plurality of crystal planes for diffracting incident radiation at the Bragg angle,
   (b) a semiconductor detector region, integrated into said crystal and having a depletion region located at a depth below a surface of said semiconductor crystal such that current in a said semiconductor detector region due to said incident radiation incident on said surface of the crystal decreases significantly when said crystal is oriented at the Bragg angle with respect to the incident radiation,
   (c) said semiconductor detector region producing said current by collecting electron-hole pairs in said depletion region, but not significantly collecting electron-hole pairs in a region closer to said surface than depletion region,
   (d) said depletion region located deeper in said crystal than the extinction length of the incident radiation at the Bragg angle, but less than the extinction length of the incident radiation at angles other than the Bragg angle, and
   (e) electrodes connected to said semiconductor detector region, said electrodes providing an electrical signal indicative of diffraction at the Bragg angle.
2. The diffraction device as recited in claim 1, wherein said semiconductor detector region comprises a p-n junction with an associated depletion region.
3. The diffraction device as recited in claim 2, wherein said semiconductor crystal is selected from the group consisting of silicon, germanium, zinc selenide, gallium arsenide and indium antimonide.
4. The diffraction device as recited in claim 1, further comprising means responsive to said electrical signal for maintaining said crystal oriented at the Bragg angle.
5. The diffraction device as recited in claim 4, wherein said maintaining means comprises an amplifier.
6. The diffraction device as recited in claim 5, wherein said maintaining means comprises a feedback circuit.

7. The diffraction device as recited in claim 1, wherein said electrode comprises a first electrode strip surrounding and in contact with an active surface area of said detector located above said semiconductor detector region and a second electrode strip forming a guard ring surrounding said first electrode strip and located outside of said active surface area.

8. A diffraction device comprising:
   (a) a crystal having a plurality of crystal planes for diffracting incident radiation at the Bragg angle,
   (b) a detector region, integrated into said crystal and located at a depth below a surface of the crystal such that electrons of said detector region due to said incident radiation incident on said surface are minimally formed in said detector region from said incident radiation when said crystal is oriented at the Bragg angle with respect to the incident radiation,
   (c) said detector region located deeper in said crystal than the extinction length of the incident radiation at the Bragg angle, but less than the extinction length of the incident radiation at angles other than the Bragg angle, and
   (d) means for detecting absorption of said incident radiation by measuring an effect of said formed electrons.

9. A diffraction device as recited in claim 8 wherein said crystal comprises an insulator and said detector region comprises an impurity which fluoresces as a result of the formation of said electrons.

10. A diffraction device as recited in claim 9 wherein said impurity comprises a metal ion.

11. A diffraction device as recited in claim 9 wherein said crystal comprises quartz or beryl.

12. A diffraction device as recited in claim 8 wherein said crystal comprises an artificially layered multi-layered surface.

* * * * *